United States Patent [19]

Henderson et al.

[11] Patent Number: 4,583,084
[45] Date of Patent: Apr. 15, 1986

[54] PATIENT MONITOR

[75] Inventors: Brooks Henderson, N. Aurora; Kevin Treu, Niles, both of Ill.

[73] Assignee: Lutheran General Hospital, Inc., Park Ridge, Ill.

[21] Appl. No.: 574,475

[22] Filed: Jan. 27, 1984

[51] Int. Cl.[4] ............................................. G08B 23/00
[52] U.S. Cl. .................................... 340/573; 340/548;
340/665; 128/134; 128/782; 200/DIG. 2;
200/153 F; 200/334
[58] Field of Search ............... 340/573, 548, 540, 546,
340/665, 668, 687, 286 R, 286 M, 568; 128/782,
774, 133, 134; 200/DIG. 2, 153 F, 61.77, 61.81,
331, 334

[56] References Cited

U.S. PATENT DOCUMENTS

| | | | |
|---|---|---|---|
| 2,784,395 | 3/1957 | Gorby | 340/573 |
| 3,618,065 | 11/1971 | Trip | 340/568 |
| 3,742,480 | 6/1973 | Hoecker | 340/568 |
| 3,911,414 | 10/1975 | Bowling | 340/548 |
| 4,020,482 | 4/1977 | Feldl | 340/573 |
| 4,024,526 | 5/1977 | Banner | 340/548 |
| 4,175,263 | 11/1979 | Triplett et al. | 340/573 |
| 4,228,426 | 10/1980 | Roberts | 340/573 |
| 4,264,904 | 4/1981 | McCoy et al. | 340/573 |
| 4,286,589 | 9/1981 | Thompson | 340/573 |
| 4,295,133 | 10/1981 | Vance | 340/573 |

Primary Examiner—Donnie L. Crosland
Attorney, Agent, or Firm—Willian Brinks Olds Hofer Gilson & Lione Ltd.

[57] ABSTRACT

A patient monitor includes an enclosure which is secured to the bed of a patient. The enclosure is electrically connected with a nurse's call panel and the enclosure serves to mount a jack which is electrically connected to the nurse's call panel. This jack includes a normally closed switch which is opened when a mating plug is installed in the jack. The plug is connected by a cord to the gown of the patient in the bed. When the patient attempts to leave the bed the patient's motion pulls the plug from the jack, thereby allowing the switch to close and signalling via the call panel the patient's attempt to leave the bed.

9 Claims, 3 Drawing Figures

PATIENT MONITOR

BACKGROUND OF THE INVENTION

The present invention is directed to a monitor which operates to trigger an alarm when a patient attempts to leave a bed.

In a hospital setting it is not uncommon for a patient to be prone to falls in leaving a bed or in attempting to walk. All too often, such a patient will not notify hospital nurses that he or she needs help, but will instead attempt to get out of bed and walk without assistance. When this happens, falls and injury to the patient may well result.

The need for a monitor to detect when a patient attempts to leave a hospital bed has been recognized for some time. For example, U.S. Pat. No. 2,784,395 to Gorby discloses a patient fall-out warning device for hospital beds in which a wire is strung over the bed. A patient attempting to leave the bed breaks the wire, thereby triggering the warning device.

A second approach of the prior art has been the use of pressure-sensitive pads either in or under the mattress of a hospital bed. U.S. Pat. No. 4,295,133 to Vance, U.S. Pat. No. 4,264,904 to McCoy, U.S. Pat. No. 4,020,482 to Feldl, and U.S. Pat. No. 4,175,263 to Triplett et al are four examples of such prior art pressure-sensitive warning systems.

The prior art approaches to this problem are not without disadvantages. The system disclosed in the Gorby patent, for example, requires the conductor to be strung over the bed. The pressure-sensitive systems described in the Vance, McCoy, Feldl, and Triplett patents are relatively complex, and they provide only an indirect indication of patient movement because they sense pressure rather than the position of the patient.

SUMMARY OF THE INVENTION

The present invention is directed to an improved patient monitor which is simple and reliable in operation and inexpensive to manufacture.

According to this invention, a patient monitor is provided for use with a call panel of the type which activates a remote alarm in response to a predetermined signal and is situated adjacent to a bed. The monitor of this invention comprises a cord having a first end and a second end. Means are coupled between the first end of the cord and the call panel for generating the predetermined signal when the cord is pulled. Furthermore, means are provided for securing the second end of the cord to clothing of the patient in the bed. The signal generating means and the cord securing means cooperate to cause the call panel to activate the remote alarm when a patient attempts to leave the bed and in so doing applies forces to the cord.

The invention itself, together with further objects and attendant advantages, will best be understood by reference to the following detailed description taken in conjunction with the accompanying drawings.

DETAILED DESCRIPTION OF THE PRESENTLY PREFERRED EMBODIMENTS

Figure 1:
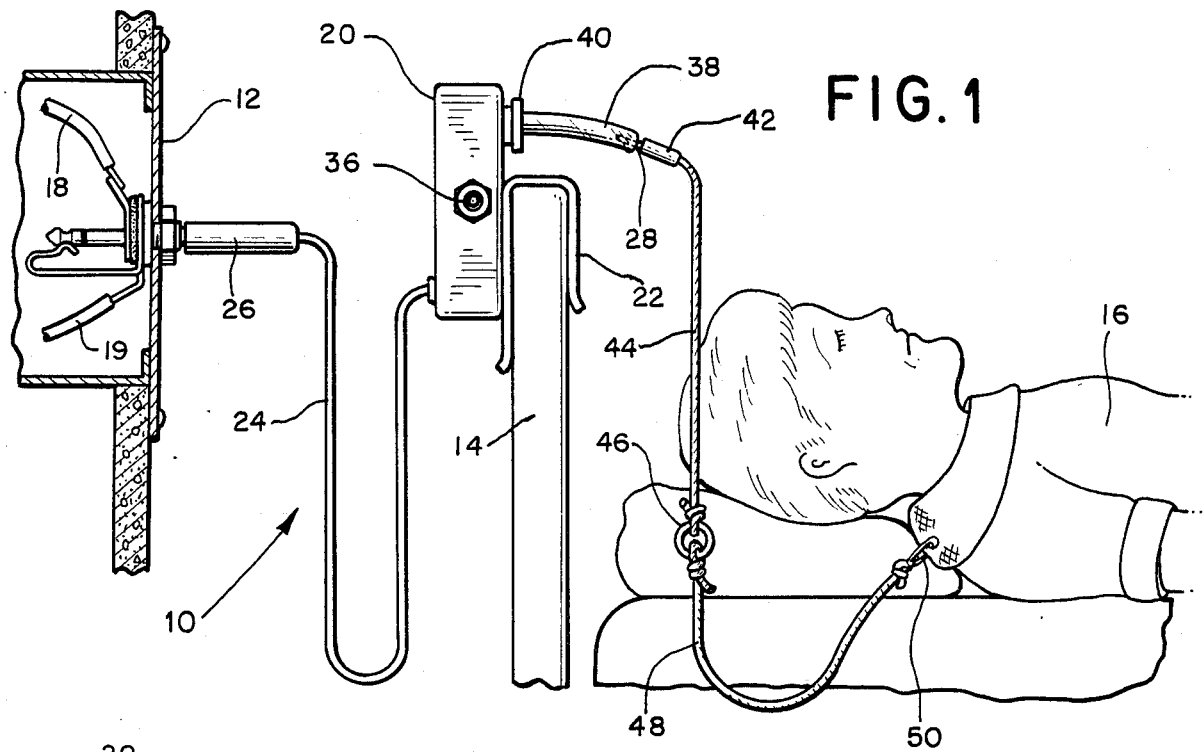
FIG. 1 is a side elevational view of a presently preferred embodiment of the monitor of this invention in use.
Figure 2:
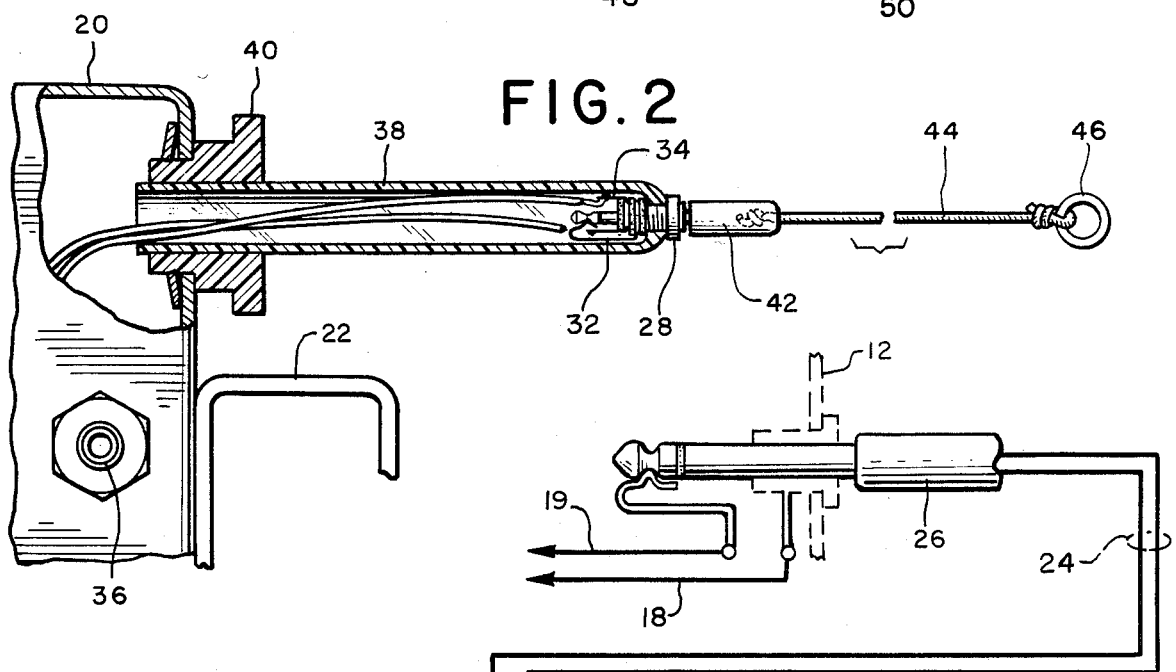
FIG. 2 is an enlarged view of portions of the monitor of FIG. 1.

Turning now to the drawings, FIG. 1 shows a side elevational view of a presently preferred embodiment 10 of the patient monitor of this invention. As shown in FIG. 1, the monitor 10 is connected to a nurse's call panel 12 situated near a hospital bed 14.

A nurse's call panel is a device well known to those skilled in the art. Typically, a large number of individual nurse's call panels, each associated with a respective hospital bed, all communicate with a central nurse's console. A lamp is provided on the central console for each of the separate call panels, and circuitry is provided which illuminates any one of the lamps when two conductors in the associated call panel are shorted together. It should be understood that the details of the call panel and the central console are well known to those skilled in the art and do not form any part per se of the present invention. For that reason, they will not be described in any greater detail here.

The monitor 10 includes an enclosure 20 which can be formed of any suitable metal, plastic, or other material. The enclosure 20 is securely mounted to a U-shaped bracket 22 which is sized to fit over and rest on the headboard of the bed 14. A cable 24 emerges from the enclosure 20, and this cable 24 is provided with a plug 26 sized to fit within a jack included in the call panel 12. In addition, the enclosure 20 serves to mount a second jack 28. The second jack 28 is secured at one end of a flexible plastic tube 38. The other end of the flexible plastic tube 38 is secured to the enclosure 20. An annular brace 40 is provided between the enclosure 20 and the flexible tube 38 to ensure that the flexible tube 38 does not pull free of the enclosure 20.

The jack 28 serves to receive a plug 42 to which is mounted a cord 44. The free end of the cord 44 is tied to a washer 46, and a length of a lightweight, easily breakable yarn 48 is also tied to the washer 46. The free end of the yarn 48 is secured by means of a safety pin 50 to the gown 16 of the patient in the bed 14. Preferably, the safety pin 50 is positioned at the upper rear portion of the gown 16, as for example near the center of the collar.

Figure 3:
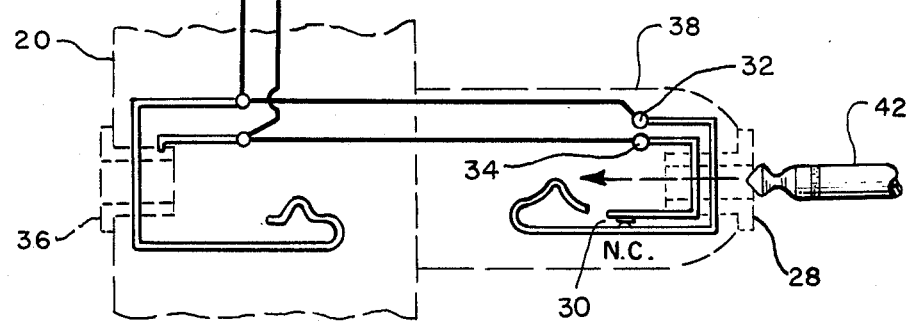
FIG. 3 is a schematic diagram of the electrical circuitry of the monitor of FIG. 1.

FIG. 3 shows an electrical schematic diagram of the monitor of FIG. 1. As shown in FIG. 3, the cable 24 includes two conductors which are connected to respective terminals 32,34 of the jack 28. The jack 28 includes a normally closed switch 30 which provides a short circuit between the terminals 32,34 whenever the plug 42 is absent from the jack 28. The switch 30 is positioned such that it is opened by the plug 42 when the plug 42 is inserted in the jack 28. The plug 42 does not itself perform any electrical function. Rather, it mechanically actuates the switch 30.

From the foregoing description it should be apparent that the monitor 10 serves to short-circuit the two conductors 18,19 of the call panel 12 whenever the plug 42 is absent from the jack 28, and to provide an open circuit between the two conductors 18,19 when the plug 42 is present in the jack 28. As explained above, the call panel 12 operates to actuate a respective lamp on a central console (not shown) when the conductors 18,19 are short-circuited. Thus, the monitor 10 causes the associated lamp to be activated whenever the plug 42 is removed from the jack 28.

The enclosure 20 also includes an auxiliary jack 36 which is connected in parallel with the jack 28. The auxiliary jack 36 allows a conventional device, such as a nurse's call button for example, to be plugged into the enclosure 20 rather than directly into the call panel 12.

In use, the monitor 10 provides a simple and reliable indication to a nursing staff as to when a patient attempts to leave the bed 14. In order to use the monitor 10, the enclosure 20 is placed on the headboard of the bed 14 and the plug 26 is plugged into the call panel 12. Then the free end of the yarn 48 is secured by means of the safety pin 50 to the upper rear portion of the gown 16 of the patient in the bed 14. The plug 42 is then placed in the jack 28.

In the event the patient attempts to leave the bed 14, the patient's movements will pull the plug 42 from the jack 28, thereby short-circuiting the conductors 18,19 and causing the associated lamp on the central console to be illuminated. This alerts the nursing staff that the patient is attempting to leave the bed, and they can then respond to assist the patient and prevent an accidental fall.

One of the important advantages of this invention is that the plug 42 is preferably secured to a rear portion of the gown of the patient such that the patient forgets about the monitor 10. Because it is the distance between the patient and the enclosure 20 that is in effect being measured by the monitor 10, the monitor of this invention is substantially immune to false alarms of the type associated with restlessness of the patient. The combined length of the cord 44 and the yarn 48 should be chosen such that during a normal range of patient movement the plug 42 remains in the jack 28, yet the plug 42 is pulled from the jack 28 before the patient is successful in leaving the bed.

The function of the breakable yarn 48 is to ensure that the patient is not trapped in the bed 14 in the unlikely event that the plug 42 cannot be removed from the jack 28. The yarn 48 should be chosen so as not to break during normal usage but to be easily breakable if necessary to free the patient.

The flexible tube 38 allows the jack 28 to move as necessary to align itself with forces applied to the jack 28 by means of the plug 42 and the cord 44. Thus, the flexible tube 38 ensures a more nearly axial application or forces to the jack 28, thereby protecting both the plug 42 and the jack 28 from damage.

Simply by way of example, and without in any way limiting the scope of this invention, the presently preferred embodiment uses a telephone plug for the plug 28, a mini-phone plug for the plug 42, a mini-phone jack for the jack 28, and a standard telephone jack for the jack 36. In this embodiment the housing 20 is formed of sheet aluminum and the flexible tube 38 is securely bonded by suitable adhesives to the brace 40 and the enclosure 20.

Of course, it should be understood that a wide range of changes and modifications to the preferred embodiment described above will be apparent to those skilled in the art. For example, the present invention can readily be adapted for other types of call panels which may, for example, activate an alarm in response to an open circuit rather than in response to a short circuit. Furthermore, differing types of plugs and sockets can be substituted as desired for those described above. Moreover, the enclosure can be mounted to the bed by other means, such as spring clips and the like, or it can be wall-mounted if desired. It is therefore intended that the foregoing detailed description be regarded as illustrative rather than limiting, and that it be understood that it is the following claims, including all equivalents which are intended to define the scope of this invention.

We claim:

1. In combination with a call panel of the type which activates a remote alarm in response to a predetermined signal and is situated adjacent to a bed, the improvement comprising:
   a cord having a first end and a second end;
   means, coupled to the first end of the cord and the call panel, for generating the predetermined signal when the cord is pulled; and
   means for securing the second end of the cord to clothing of a patient in the bed;
   said cord, generating means, and securing means cooperating to cause the call panel to activate the remote alarm when a patient attempts to leave the bed.

2. The invention of claim 1 wherein the generating means comprises:
   a plug connected to the first end of the cord;
   an enclosure;
   a socket mounted on the enclosure and sized to receive the plug;
   a cable interconnecting the socket with the call panel; and
   means for generating the predetermined signal when the plug is absent from the socket.

3. The invention of claim 2 wherein the socket is mounted to the enclosure by an elongated flexible member such that the orientation of the socket is variable in response to forces applied to the socket by the cord.

4. The invention of claim 3 wherein the flexible member comprises a resilient tube secured at one end to the enclosure and at the other end to the socket.

5. The invention of claim 1 wherein the means for securing the second end of the cord to clothing of a patient comprises an easily broken, lightweight length of material.

6. In combination with a call panel of the type which activates a remote alarm in response to a predetermined signal and is situated adjacent to a hospital bed, the improvement comprising:
   a cord having a first end and a second end;
   a plug connected to the first end of the cord;
   means for securing the second end of the cord to clothing of a patient in the bed;
   a jack sized to receive the plug, said jack having two terminals which are shorted together when the plug is absent from the jack and are open circuited when the plug is in the jack;
   an enclosure;
   a flexible tube having a first end secured to the jack and a second end mounted to the enclosure such that the jack moves in response to forces applied via the cord to more nearly align the jack with said forces;
   means for securing the enclosure to the bed;
   conductor means which pass through the tube for electrically interconnecting the call panel with the two terminals of the jack;
   said call panel responsive to a short circuit between the two terminals of the jack to activate the remote alarm when a patient pulls the plug out of the jack in attempting to leave the bed.

7. The invention of claim 2 wherein the generating means further comprises an additional socket mounted on the enclosure, said additional socket comprising two terminals which are normally open circuited and capable of generating the predetermined signal when said terminals are close circuited.

8. The invention of claim 1 wherein the improvement further comprises means for detachably securing the enclosure to the bed.

9. The invention of claim 8 wherein the securing means comprises a U-shaped bracket.

* * * * *